United States Patent [19]

Tseo

[11] Patent Number: 4,747,828
[45] Date of Patent: May 31, 1988

[54] IV FLUID LINE OCCLUSION DETECTOR

[75] Inventor: Gus G. Tseo, San Diego, Calif.

[73] Assignee: Fisher Scientific Group, San Diego, Calif.

[21] Appl. No.: 939,549

[22] Filed: Dec. 9, 1986

[51] Int. Cl.⁴ .............................................. A61M 31/00
[52] U.S. Cl. ........................................ 604/67; 417/20;
   417/38; 417/43; 604/152; 604/121
[58] Field of Search .............. 604/245, 121, 50, 67,
   604/118, 244, 151–155; 417/20, 38, 43

[56] References Cited
U.S. PATENT DOCUMENTS

| | | | |
|---|---|---|---|
| 3,631,847 | 1/1972 | Hobbs, II | 604/67 |
| 3,985,133 | 10/1976 | Jenkins | 604/152 |
| 4,244,365 | 1/1981 | McGill et al. | 128/214 E |
| 4,277,226 | 7/1981 | Archibald | 417/38 |
| 4,277,227 | 7/1981 | Jenkins | 417/63 |
| 4,286,925 | 9/1981 | Standish | 417/12 |
| 4,373,525 | 2/1983 | Kobayashi | 128/214 |
| 4,391,599 | 7/1983 | Jenkins | 604/118 |
| 4,392,847 | 7/1983 | Whitney et al. | 604/118 |
| 4,450,079 | 5/1984 | Farr | 604/152 |
| 4,544,369 | 10/1985 | Skakoon et al. | 604/245 |
| 4,617,014 | 10/1986 | Cannon et al. | 604/67 |

Primary Examiner—Stephen C. Pellegrino
Assistant Examiner—Colleen Reilly
Attorney, Agent, or Firm—Workman, Nydegger & Jensen

[57] ABSTRACT

A detector for determining when an occlusion has occurred in the fluid line of an IV administration set comprises means associated with an IV infusion pump to determine the resistive force exerted by fluid in the line against the pumping mechanism of the pump. The detector includes a flexible beam which is mounted between the plunger and the activator of the pumping mechanism and which bends proportionately to the magnitude of the resistive force. A strain gauge attached to the beam activates an alarm which stops the IV pump when flexure of the beam indicates an occlusion in the line has occurred.

19 Claims, 2 Drawing Sheets

IV FLUID LINE OCCLUSION DETECTOR

BACKGROUND OF THE INVENTION

The present invention relates to devices which are useful in the operation and control of systems that regulate fluid flow. More particularly the present invention pertains to a detector which can sense fluid pressure in a line through which fluid is being pumped. The present invention is particularly, but not exclusively, useful in the health care field for indicating when the intravenous administration of medical solutions to patients has become impared by an occlusion in the IV line.

DESCRIPTION OF THE PRIOR ART

Intravenous (IV) infusion therapy is a widely accepted procedure for many medical complications. As is to be expected, such therapy frequently involves infusing highly potent medications to a patient. While this fact alone is sufficient to require a precisely controlled procedure, the actual concern is much broader in scope. Even when relatively harmless solutions are being infused, the procedure must still be dependably accomplished with care and accuracy. Accordingly, the systems used for IV therapy must include precision instruments which are both durable and reliable.

In IV therapy, the dosage and efficacy of the medical solutions infused to the patient are important considerations. They are not, however, the only considerations. Aside from the pharmacological properties of the drugs being infused, the mechanical characteristics and capabilities of the IV administation device can be of great concern. Specifically, the particular concern of the present invention is for those problems which are directly related to an undesirable build up of fluid pressure in the system. Such problems are well known. Accordingly, there is a recognized need for an IV administration device which dependably infuses medical solutions at safe pressures that will not traumatize the patient or uncontrollably infuse the patient with a potentially harmful bolus of a high potency drug. As will be appreciated, both of these unwanted effects can result in an occlusion or blockage of the line that causes a build up of fluid pressure.

The occlusion or blockage can be caused in any number of ways. For instance, an IV line occlusion can be caused by the inadvertent failure to release a clamp on the line or by a crimping of the line such as when the patient rolls over the line. On the other hand, the occlusion might be caused by improper needle placement such as would be caused if the needle is inserted into a muscle rather than into a vein. Regardless of the cause, either a build up of high fluid pressure or the sudden release of high fluid pressure can be potentially harmful to the patient. Thus, it is important that the IV administration device be shut down whenever an occlusion or blockage in the line prevents proper infusion of solutions to the patient.

Several devices have been disclosed which are intended to help solve these problems by providing a warning whenever high fluid pressures are encounterd in the IV fluid line. For example, U.S. Pat. No. 4,373,525 to Kobayashi discloses a device for this purpose which correlates fluid pressure to dimensional variations in the outer diameter for the tubing used for the IV line. Another example is U.S. Pat. No. 4,244,365 to McGill et al. which discloses a device that monitors for excessive pressure in the set by using an optical sensor to detect the fluid level in a closed pressure chamber. Also, U.S. Pat. No. 4,277,227 to Jenkins discloses a device having a resilient diaphragm disposed in the fluid line whose movement is measured as an indication of fluid pressure in the line. Significantly, the aforementioned devices were all designed with the unique problems of IV therapy in mind. They all, however, employ pressure sensing members which are structurally independent of the actual pumping mechanism. This is somewhat understandable when considering that IV administration sets must deal with relatively flow fluid pressures and very small fluid pressure differentials. With this in mind, a logical point for taking such measurements is directly from the IV fluid line. Such a connection, however, may not be as direct as first assumed. In each of the above-cited references some additional member or device is incorporated into the system which can introduce unwanted errors into the pressure reading.

An alternative to connecting the pressure sensing device with the IV fluid line is to connect the device directly to the pumping mechanism. If positioned on the pumping mechanism in direct opposition to the fluid's resistive force, a pressure sensing device is able to detect the actual force required to pump fluid through the system. This force is, of course, directly proportional to the fluid pressure in the system since the fluid pressure manifests itself as the resistive force counteracting the pumping force. The present invention recognizes that an arrangement which takes advantage of this fact can be applied in an IV administration system. Although the invention disclosed in U.S. Pat. No. 4,286,925 to Standish provides for a load transducer connected to the polished rod of a well pump, Standish does not teach or suggest an apparatus that is appropriate for use in IV therapy. Indeed, to contrast the Standish apparatus with the present invention, it can be appreciated that the environments are quite different and that the forces involved are of incomparable orders of magnitude.

In light of the above, it is recognized there is a need for a fluid pressure detector having enhanced accuracy which can be easily incorporated into an IV administration system. Further, there is a need for an uncomplicated fluid pressure detector which is reliable and durable.

Accordingly, it is an object of the present invention to provide a fluid pressure detector for use in IV therapy which will accurately determine when an occlusion has occurred in the fluid line. Another object of the present invention is to provide an occlusion detector which is associated directly with the pumping mechanism of an IV infusion pump. Still another object of the present invention is to provide an occlusion detector which is sensitive to small variations in fluid pressure at relatively low fluid pressure levels. Yet another object of the present invention is to provide an IV line occlusion detector which is reliable and durable. It is yet another object of the present invention to provide a fluid pressure sensor which can be easily manufactured and which is cost effective.

SUMMARY OF THE INVENTION

The preferred embodiment of the novel IV fluid line occlusion detector of the present invention comprises a plunger disposed for movement within the pumping chamber of an IV infusion pump. The detector also comprises a motor driven carriage. Connected between the plunger and carriage is a flexible beam having its longitudinal axis generally aligned perpendicular to the direction of travel for the plunger. A strain gauge is mounted on the beam to measure its flexural deflections. Since the plunger is in direct contact with the fluid being pumped through the system, the flexural deflections measured by the strain gauge are indicative of the fluid pressure in the IV line. The detector of the present invention also comprises an alarm which is connected with the strain gauge to alarm and stop the operation of the IV pump whenever beam deflections indicate a fluid pressure which evidences an occlusion of the line.

The novel features of this invention as well as the invention itself, both as to its organization and operation, will be best understood from the accompanying drawings taken in conjunction with the accompanying description in which similar reference characters refer to similar parts and in which:

BRIEF DESCRIPTION OF THE PREFERRED EMBODIMENT

Figure 1:
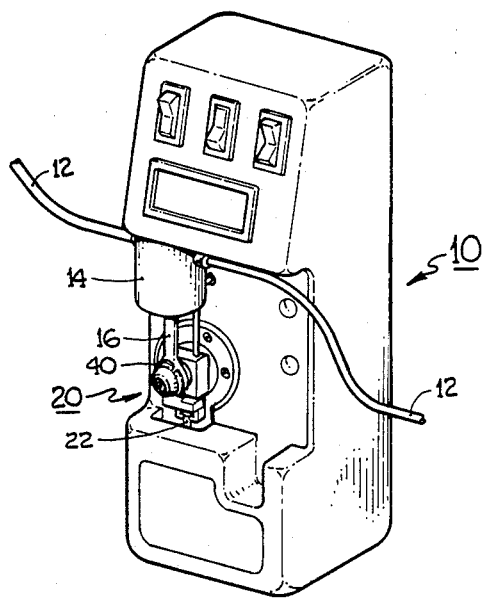
FIG. 1 is perspective view of a volumetric IV pump employing the occlusion detector of the present invention.

Referring initially to FIG. 1, an IV volumetric pump generally designated 10 is shown in operative association with a fluid line 12. As is well known by those skilled in the art, an IV pump 10 can be used for pumping fluids through a fluid line 12 for the purpose of infusing medical solutions to a patient. Typically, an IV pump 10 of this type incorporates a pumping chamber 14 which is operatively engaged with a piston 16. A drive shuttle 42 is mounted for reciprocal movement on IV pump 10 and is clampingly engaged with piston 16. The operation of an IV pump incorporating structures similar to that envisioned for the pumping mechanism of IV pump 10 as disclosed in U.S. Pat. No. 3,985,133 which is assigned to the assignee of the present invention and which is incorporated herewith.

The occlusion detector generally designated 20 in FIG. 1 is associated with an actuator 22 such that reciprocal movement of the actuator 22 is transferred through the mechanical structure of occlusion detector 20 for movement of drive shuttle 42. As will be appreciated, the connection of drive shuttle 42 with the piston 16 causes the pumping action of piston 16 within fluid chamber 14 for operation of the IV pump 10.

Figure 2:
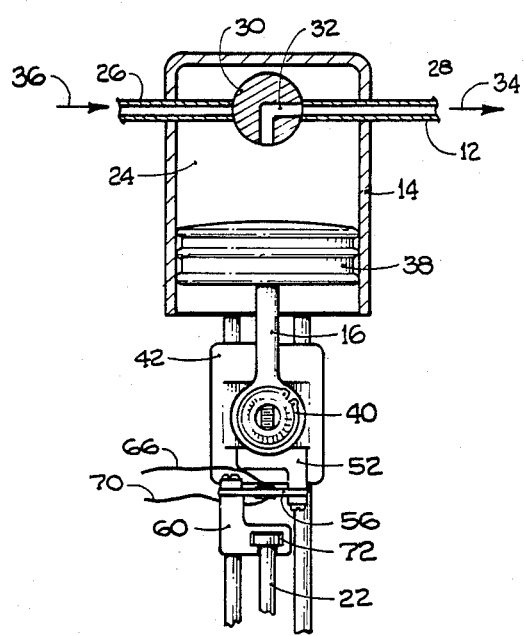
FIG. 2 is a front elevational view of the occlusion detector shown inoperative engagement with the pumping chamber of a volumetric IV pump with portions shown in cross-section for clarity.

A clearer understanding of the mechanism for pumping medical solutions through the IV pump 10 is obtained by reference to FIG. 2. As seen in FIG. 2, pumping chamber 14 is established with an interior 14 for receiving fluids therein. Pumping chamber 14 is also provided with an inlet 26 which connectable in fluid communication with the fluid line 12. Additionally, pumping chamber 14 is formed with an outlet 28 which is adapted for connection into fluid communication with fluid line 12.

As seen in FIG. 2, IV pump 10 incorporates a valve 30 which is formed with an L-shaped groove 32. Through a mechanism (not shown), such as the one disclosed in U.S. Pat. No. 3,985,133, IV pump 10 coordinates the rotation of valve 30 to alternately provide fluid communication between either inlet 26 or outlet 28 and interior 24. As shown in FIG. 2 any advancement of piston 16 that moves the plunger 38 into the interior 24 of pumping chamber 14 will cause fluid within interior 24 to be expelled through groove 32 and outlet 28 and in the direction of arrow 34 into fluid line 12. As mentioned above, valve 30 is mounted in IV pump 10 for rotational movement between its position as shown in FIG. 2 and a position wherein the L-shape groove 32 establishes fluid communication between inlet 26 and interior 24. When L-shaped groove 32 is established in this latter described orientation a withdrawal of plunger 38 from the interior 24 causes fluid from a source (not shown) to move in the direction of arrow 36 through inlet 26 and into interior 24.

As will be appreciated by the skilled artisan, the actual pumping operation of IV pump 10 is accomplished by coordinating the reciprocal movement of plunger 38 with the rotational position of valve 30. Again, more precise description of such an operation is found in U.S. Pat. No. 3,985,133.

Figure 3:
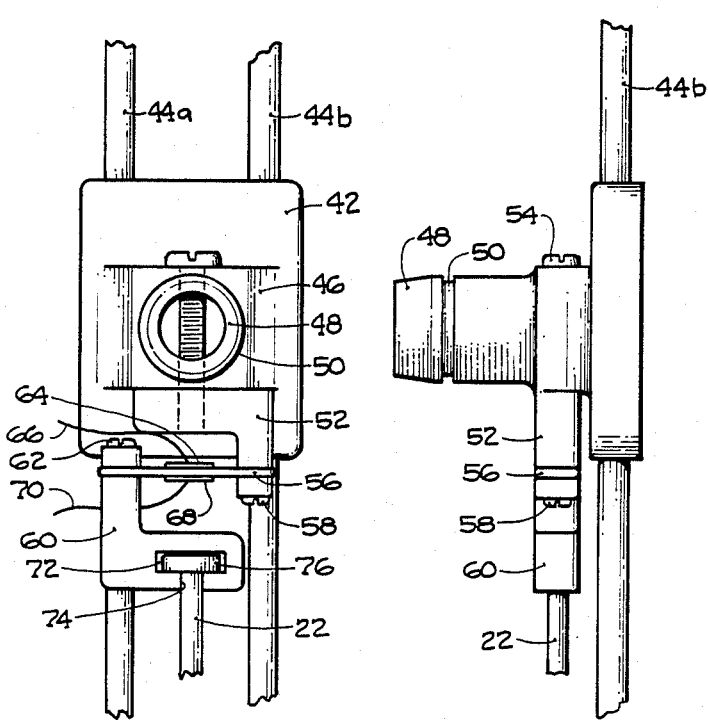
FIG. 3 is a front elevational view of the occlusion detector connected with the drive shuttle of a volumetric IV pump.

Referring now to FIG. 3, it can be seen that IV pump 10 incorporates a shuttle 42 which is slidingly mounted on a pair of guide rails 44a and 44b. Guide rails 44a and 44b are aligned in a substantially parallel manner to establish a linear reciprocal movement of shuttle 42. Shuttle 42 also is formed with abutment 46 from which shuttle nose 48 extends. Shuttle nose 48 is formed with a detent 50 which is engageable with a coupler 40. As seen in FIGS. 1 or 2, coupler 40 is formed as an extension of piston 16. It will be appreciated that upon engagement of coupler 40 with shuttle 42, the linear reciprocal motion of shuttle 42 is transmitted as a linear reciprocal motion to piston 16 and plunger 38 for a purpose as previously described in the pumping operation of IV pump 10. A bracket 52 is fixedly attached to shuttle 42 by any manner well known in the art, such a by use of a bolt 54. As seen in FIG. 3, a beam 56 is fixedly attached to bracket 52 in any manner well known in the art such as by bolt 58. A support 50 is fixedly attached to the beam 56 at the end of beam 56 which is opposite from its point of attachment to the bracket 52. The engagement of carriage 60 with beam 56 can be accomplished by any means, such as by bolt 62.

As best shown in FIG. 3, it can be appreciated that, beam 56 is positioned in a manner which places the longitudinal axis of beam 56 in a substantially perpendicular orientation with respect to direction of travel for shuttle 42. As also seen in FIG. 3, a strain gauge 64 is attached to the upper surface 56. Further, wiring 66 is used to make an electrical connection between strain gauge 64 and an alarm means (not shown) which incorporates electronic circuitry well known in the pertinent art. The particular strain gauge for use in the present invention can be of any type well known in the art which will determine or react to fluctures of the beam 56.

It will also be noticed in FIG. 3 that a strain gauge 68 is attached to the under surface of beam 56. Again, the strain gauge 68 is connected with wiring 70 which may also be used for connection with the alarm means (not shown). It is recognized by the present invention that the incorporation of both strain gauge 66 and strain gauge 68 provides for redundancy in the system.

Figure 4:
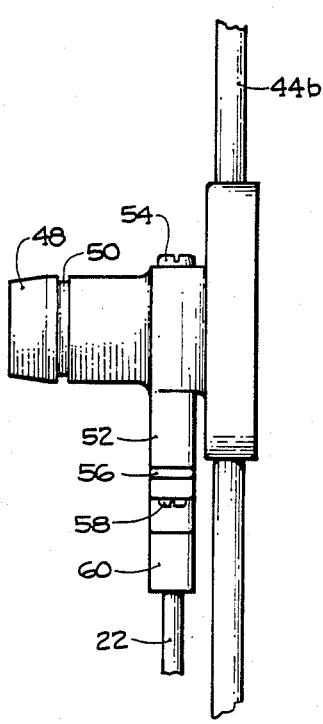
FIG. 4 is a side view of the occlusion detector seen in FIG. 3.

As shown in FIGS. 2 and 3, carriage 60 is formed with a T-shaped notch 72. It is to be appreciated; however, that the particular shape of notch 72 is somewhat unimportant since its purpose is to provide an attachment point between actuator 22 and carriage 60. As specifically seen in FIG. 3, T-shaped notch 72 has a stem 74. The void thus formed by T-shaped notch 72 allows for an engagement of carriage 60 with a flange 76 which is fixedly attached or formed as part of the actuator 22. Actuator 22 is in turn connected to a drive means (not shown) which provides the power for a linear reciprocal movement of actuator 22. The further cooperation of shuttle 42 with guide rails 44 and the interconnections between actuator 22 and shuttle 42 through bracket 52 and support 60 is seen by cross-reference FIG. 3 with FIG. 4.

Figure 5:
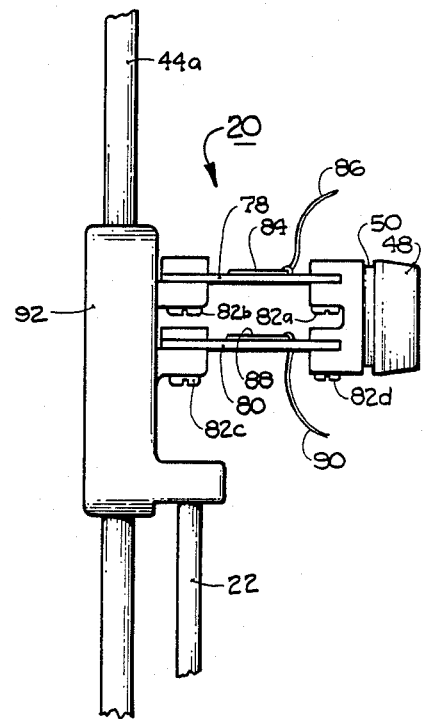
FIG. 5 is a side view of an alternative embodiment of an occlusion detector.

FIG. 5 shows an alternate embodiment for the present invention which can be used with an IV pump 10. More specifically, the invention as shown in FIG. 5 transfers the occlusion detector 20 from a position where it is located between actuator 22 and shuttle 42 to a location where the occlusion detector 20 is established between a modified shuttle 92 and piston 16 of IV pump 10. As shown in FIG. 5, this rearrangement of elements can be accomplished by fixedly attaching an upper beam 78 between the modified shuttle 92 and the shuttle nose 48. Likewise, a lower beam 80 can be positioned between modified shuttle 92 and shuttle nose 48. As will be appreciated by the skilled artesan, both upper beam 78 and lower beam 80 can be connected between these structures by any means well known in the art such as by bolts 82a, 82b, 82c, and 82d.

In a manner similar to that discussed above with respect to the strain gauges 64, 68, upper beam 78 is provided with a strain gauge 84 and associated wiring 86. Likewise lower beam 80 is associated with strain gauge 88 and its associated wiring 90. Again, the present invention recognizes that the incorporation of an upper beam 78 and a lower beam 80 provides for redundancy and that either one of the beam could function for the particular purposes of IV pump 10. Accordingly, beams 78 and 80 are oriented with respect to the pumping mechanism of the alternate embodiment, in a manner similar to that previously described for beam 56, with their longitudinal axes substantially perpendicular to the direction in which shuttle 42 is reciprocated. In this manner, the resistive force created by fluid in the system is directly transferred from plunger 38 back through piston 16 and onto shuttle nose 48 where it will cause a bending or flexure of beams 78 and 80. As is well known by the skilled artesan, flexures of beam 56 in the preferred embodiment, or of beams 78 and 80 for the alternate embodiment, are indicative of the amount of bending force applied to the respective beams. The strain gauges 64, 84 and 88, as described, are connected in operative contact with the respective beams for purposes of measuring this flexure and generating electronic signals via the associated wirings to an alarm means which is programmed, in a manner well known in the pertinent art, to cause a stoppage of IV pump 10 in the event an excessive force is detected by the occlusion detector 20.

Figure 6:
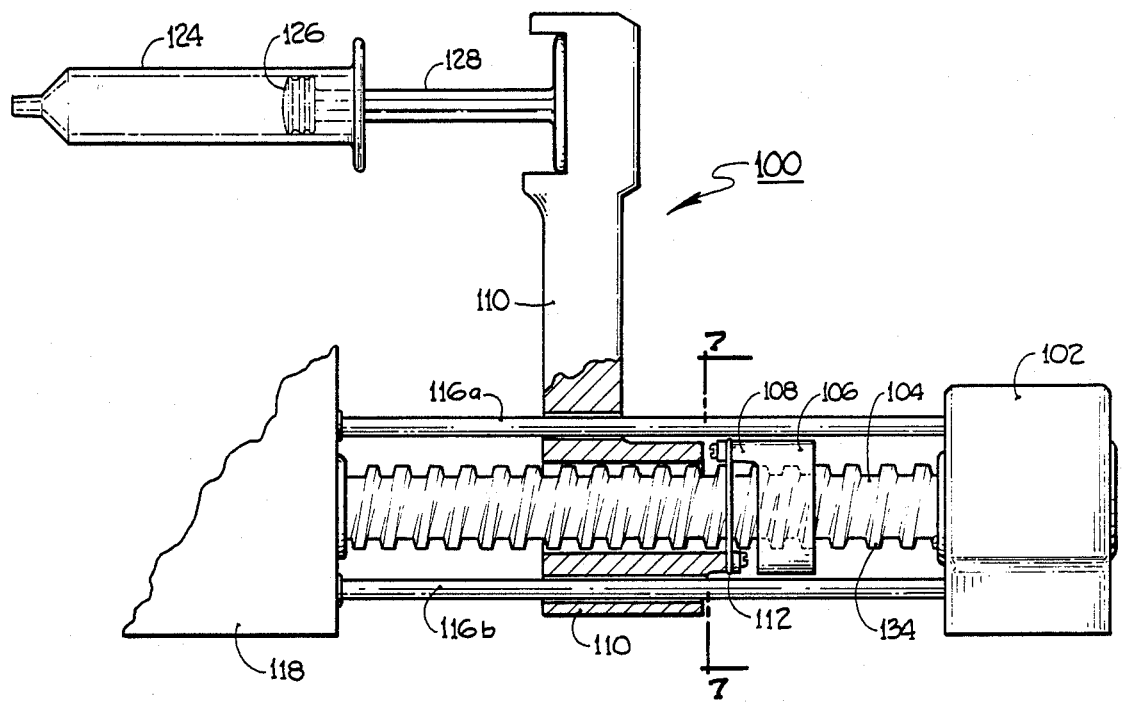
FIG. 6 is a side elevational view of the occlusion detector shown in combination with a lead screw driven syringe pump, with portions broken away for clarity.

The occlusion detector of the present invention is also adaptable for use with a syringe pump generally designated 100 in FIG. 6. Referring now to FIG. 6 it is seen that when a detector is incorporated into a syringe pump, a motor 102 is operably connected with a lead screw 104. A nut 106, which functions for the syringe pump 100 in a manner similar to carriage 60 previously described in combination with IV pump 10, is threadably engaged with lead screw 104 in a manner which will cause linear movement of nut 106 in the axial direction of lead screw 104 upon rotation of lead screw 104 by motor 102. As shown in FIG. 6, nut 106 is formed with a bracket 108 which is fixedly attached to beam 112 by any manner well known in the pertinent art, such as by bolting beam 112 onto bracket 108. Beam 112 is also fixedly attached to a pusher 110. Pusher 110 is slidably mounted on the guide rails 116a, b, c, and d to constrian pusher 110 to a linear movement substantially in the direction established by the longitudinal axis of lead screw 104. Thus, the guide rails 116a, b, c, and d are respectively attached to motor 102 and support 118 to establish the path for movement of pusher 110 as described.

Figure 7:
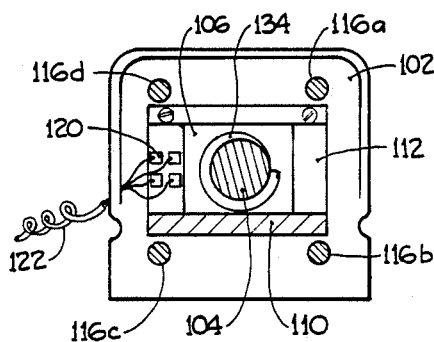
FIG. 7 is a cross-sectional view of the occlusion detector as seen along the line 7—7 in FIG. 6.

A second beam 114, as shown in FIG. 7, can be mounted between bracket 108 and pusher 110 in a manner similar to the attachment of beam 112 therebetween. The incorporation of second beam 114 is to provide for redundancy and the symmetrical generation of forces between the nut 106 and carriage 110. In FIG. 7 it will be seen that beam 114 is provided with a strain gauge 120 and its associated wiring 122. It is to be understood, though not shown in FIG. 7, that beam 112 may likewise be provided with strain gauges and associated wiring. The incorporation of strain gauges 120 onto beam 114 is accomplished in a manner previously discussed in relation to beam 56 of IV pump 10. Further, the strain gauges 120 are for a similar purpose. Specifically, any flexures of beam 114 caused by the force generated between nut 106, pusher 110 and beam 112 will be indicative of the magnitude of such force. Thus the flexure can be used to create a signal which passes through an associated alarm means (not shown) for the purpose of reacting forces in excess of a predetermined maximum.

Returning now to FIG. 6, it can be seen that the movement of pusher 110 creates a force on syringe 124. More specifically, the movement of pusher 110 causes a like movement of handle 128 and advances plunger 126 into syringe 124 for the purpose of expelling fluids from syringe 124.

Figure 8:
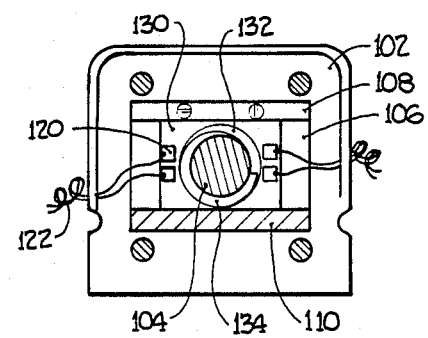
FIG. 8 is a cross-sectional view of an alternate embodiment of the occlusion detector as seen along the line 7—7 in FIG. 6.

It will be appreciated by the skilled artesan that beams 112 and 114 can be replaced by a plate 130 similar to the one shown in FIG. 8. The plate 130 is mounted between nut 106 and carriage 110 in a manner previously discussed. As seen in FIG. 8, plate 130 is formed with a hole 132 which provides sufficient clearance for the threads 134 of lead screw 104 to pass through hole 132. This arrangement, like the arrangement for the parallel displaced beams 112 and 144, is necessitated by the fact that nut 106 must travel in a linear direction along the longitudinal axis of lead screw 104.

OPERATION

In the operation of the present invention it will be appreciated by reference to FIG. 2 that linear reciprocal motion of actuator 22 will cause a similar motion of the carriage 60. Further, through the connection of carriage 60 with shuttle 42, by way of the beam 56, the reciprocal linear movement of actuator 22 will manifest itself in a like movement of the shuttle 42. More specifically, the constraining effect of the guide rails 44 on shuttle 42 ensure that shuttle 42 moves along a linear path. Consequently, piston 16 and its associated plunger 38 are moved in a linear reciprocal manner for the purpose of pumping fluids through pumping chamber 14 in a manner previously discussed.

It will be understood by the skilled artesan that the resistive force against plunger 48 caused by fluid within the interior 14 of pumping chamber 14 will manifest itself as a resistive force against the overall drive mechanism of IV pump 10. Specifically, because all other components of the drive chain are capable of maintaining a fixed relationship, any distortion caused by forces in the overall drive mechanism will result in a flexuring or bending of beam 56. It will be appreciated by the skilled artesan that the flexures of beam 56 can be turned into electronic signals through appropriately positioned strain gauges 64 and 68 mounted on beam 56 for the purpose of quantifying the resistive force of the fluid against plunger 38.

Alarm means (not shown) are electronically connected to the strain gauges 64 and 68 which are mounted on beam 56 for the purpose of providing electronic signals to the IV pump 10 and ceasing operation of the IV pump 10 in the event that resistive forces are encountered which exceed a predetermined maximum. This predetermined maximum amounts to a substantial equivalent of an occlusion in the line.

In the alternate embodiment of the occlusion detector 20 used for IV pump 10, as shown in FIG. 5, the occlusion detector 20 can be positioned between modified shuttle 92 and the shuttle nose 48 which is in direct connection with piston 16 of IV pump 10. In all important respects the flexures of upper beam 78 and lower beam 80 are used for determining when an occlusion has occurred in a manner previously discussed.

For the operation of a syringe pump 100, wherein a lead screw 104 is used for the purpose of generating the driving force, it can be seen in reference to FIG. 6 that motor 102 causes rotation of lead screw 104. This rotation acts through threads 134 on lead screw 104 to advance or retract the nut 106 in a direction along the longitudinal axis of lead screw 104. The connection of nut 106 with pusher 110 through beam 112 and beam 114, transfers linear movement of nut 106 into a linear translational movement of pusher 110. The movement of pusher 110 is constrained by its cooperation with the guide rails 116a, b, c, and d. It will be appreciated, of course, that not all four guide rails 116a, b, c, and d need be used and that the axle movement of pusher 110 can be properly constrained through the use of only two such guide rails. As pusher 110 is advanced, its translation results in a pushing force against handle 128 of syringe 124 for the purpose of advancing plunger 126 into the syringe 124 to expel fluid therefrom.

For the combination of the occlusion detector with a syringe pump 100 as herein discussed, the strain beam arrangement can be modified. In place of substantially parallel beams 112 and 114, plate 130 can be used. It will be appreciated by the skilled artesan that the importance of the connection between nut 16 and pusher 110 is to provide for the flexure of bending members such as beams 112 and 114 or plate 130 in a symmetrical relationship relative to the longitudinal axis of lead screw 104. In this manner the resistive force of fluids within the syringe 124 is transmitted back through the beam 112 and its flexures can be taken as a proper representation of the resistive force encountered by the syringe pump 100 as it expels fluid from the syringe 124.

While the particular occlusion detectors as herein shown and disclosed in detail are fully capable of obtaining the objects and providing the advantages hereinbefore stated, it is to be understood that they are merely illustrative of the presently preferred embodiments of the invention and that no limitations are intended to the details of construction or design herein shown other than as defined in the appended claims.

I claim:
1. An occlusion detector in combination with a fluid line for use with an IV administration system which comprises:
   means associated with said fluid line for pumping fluid therethrough;
   an actuator for driving said pumping means;
   a beam operatively connecting said actuator to said pumping menas, said beam being positioned to flex in proportion to the resistive force transmitted by the fluid against said pumping means;
   means mounted on said beam for measuring the flexure of said beam; and
   means connected with said measuring means for stopping said pumping means when the flexure of said beam indicates a resistive force of predetermined value.

2. An occlusion detector as recited in claim 1 wherein said beam flexure measuring means is a strain gauge.

3. An occlusion detector as recited in claim 2 further comprising means for constraining said pumping means to substantially linear movement.

4. An occlusion detector as recited in claim 3 further comprising an actuator for driving said pumping means.

5. An occlusion detector as recited in claim 4 wherein said beam has a first end and a second end with said first end mounted on said pumping means and said second end mounted on said actuator.

6. An occlusion detector as recited in claim 5 wherein said beam is positioned with its longitudinal axis substantially perpendicular to the direction of linear movement of said pumping means.

7. An occlusion detector as recited in claim 6 wherein said pumping means is disposed for reciprocal linear movement with said actuator.

8. An occlusion detector as recited in claim 7 wherein said pumping means is disposed for reciprocal linear movement with said actuator.

9. An IV fluid line occlusion detector which comprises:
   a pumping chamber in fluid communication with said fluid line;
   a plunger disposed within said chamber;
   an actuator for moving said plunger to pump fluid through said chamber;
   a flexible beam having a first end attached to said plunger and a second end attached to said actuator;

means mounted on said beam for measuring means to alarm when said beam obtains a predetermined deflection.

10. An IV fluid line occlusion detector as recited in claim 9 wherein said actuator is positioned for colinear movement with said plunger.

11. An IV fluid line occlusion detector as recited in claim 10 wherein said measuring means is a strain gauge.

12. An IV fluid line occlusion detector as recited in claim 11 wherein said beam is positioned with its longitudinal axis substantially perpendicular to the direction of linear movement of said plunger and said actuator.

13. An IV fluid line occlusion detector as recited in claim 12 wherein said plunger is disposed for reciprocal movement within said chamber.

14. An occlusion detector, in combination with a fluid line, for use with an IV administration system which comprises:
 means in operative contact with fluid in said line to pump the fluid therethrough;
 means for driving said pumping means;
 means connected between said drive means and said pumping means to measure the force therebetween when fluid is being pumped through said line; and
 means operatively connected with said measuring means to stop said IV administration system when the force between said actuator and said pumping means reaches a predetermined value.

15. An occlusion detector as recited in claim 14 further comprising a flexible beam having a first end mounted on said pumping means and a second end mounted on said drive means.

16. An occlusion detector as recited in claim 15 wherein said measuring means is mounted on said beam.

17. An occlusion detector as recited in claim 16 wherein said measuring means is a strain gauge.

18. An occlusion detector as recited in claim 17 wherein said drive means and said pumping means are disposed for colinear movement.

19. An occlusion detector as recited in claim 17 wherein said pumping means is disposed for reciprocal movement relative to said fluid line.

* * * * *